(12) United States Patent
Rohde

(10) Patent No.: US 10,796,446 B2
(45) Date of Patent: Oct. 6, 2020

(54) DETERMINING THE RELATIVE POSITION BETWEEN A THERMAL CAMERA AND A 3D CAMERA USING A HYBRID PHANTOM

(71) Applicant: Brainlab AG, Munich (DE)

(72) Inventor: Daniel Rohde, Garching (DE)

(73) Assignee: BRAINLAB AG, Munich (DE)

( * ) Notice: Subject to any disclaimer, the term of this patent is extended or adjusted under 35 U.S.C. 154(b) by 193 days.

(21) Appl. No.: 16/094,002

(22) PCT Filed: Sep. 6, 2017

(86) PCT No.: PCT/EP2017/072360
§ 371 (c)(1),
(2) Date: Oct. 16, 2018

(87) PCT Pub. No.: WO2018/215078
PCT Pub. Date: Nov. 29, 2018

(65) Prior Publication Data
US 2020/0273199 A1    Aug. 27, 2020

(30) Foreign Application Priority Data

May 23, 2017 (WO) ................. PCT/EP2017/062384

(51) Int. Cl.
*G06T 7/73* (2017.01)

(52) U.S. Cl.
CPC ...... *G06T 7/73* (2017.01); *G06T 2207/10028* (2013.01); *G06T 2207/30244* (2013.01)

(58) Field of Classification Search
CPC .. G06T 7/73; G06T 7/593; G06T 7/80; G06T 7/13; G06T 7/194; G06T 7/246;

(Continued)

(56) References Cited

U.S. PATENT DOCUMENTS 5,691,921 A    11/1997  Berlin
7,298,869 B1 *  11/2007  Abernathy ........... G06K 9/0063
                                              324/323

(Continued)

FOREIGN PATENT DOCUMENTS

CN         104408729 A     3/2015
EP           1563799 A1    8/2005

OTHER PUBLICATIONS

Höfer et al., "Infrared deflectometry for the inspection of diffusely specular surfaces", Article, Adv. Opt. Techn. 2016; 5 (5-6): pp. 377-387, published by De Gruyter., DE.

(Continued)

*Primary Examiner* — Michael S Osinski
(74) *Attorney, Agent, or Firm* — Tucker Ellis LLP

(57) ABSTRACT

A hybrid phantom including a planar surface that includes a background surface having one of a first property and a second property, and a plurality of marker surfaces. Each marker surface of the plurality of marker surfaces having the other one of the first property and the second property. The first property involves having a high thermal emissivity of 0.8 or higher and the second property involves having a low thermal emissivity of 0.2 or less. One of the first property and the second property further involves being diffuse reflective and the other one of the first property and the second property further involves being specular reflective. A method using a system comprising the hybrid phantom, a first, thermal camera, a second, three-dimensional (3D) camera, and a computer.

20 Claims, 10 Drawing Sheets

(58) Field of Classification Search
CPC ... G06T 7/85; G06T 7/70; G06T 2207/10048;
G06T 2207/10024; G06T 2207/10028;
G06T 2207/30204; G06T 2207/10012;
H04N 5/33; H04N 5/332; H04N 5/2256;
H04N 5/3651; H04N 13/271; H04N
13/239; H04N 13/254; H04N 13/128;
H04N 13/243; H04N 13/25; H04N
13/257; H04N 13/275; H04N 13/296;
G06K 9/0063; G06K 2009/2045; G06K
2009/00644; G06K 2009/00932
See application file for complete search history.

(56) References Cited

U.S. PATENT DOCUMENTS

| | | | |
|---|---|---|---|
| 7,688,998 | B2 | 3/2010 | Tuma et al. |
| 9,681,066 | B2* | 6/2017 | Strandemar ............... H04N 5/33 |
| 9,733,081 | B2* | 8/2017 | Zimmermann .......... G01C 7/00 |
| 9,941,752 | B2* | 4/2018 | Bell ........................ G01S 15/06 |
| 9,971,455 | B2* | 5/2018 | Nishioka ................ G06F 3/0416 |
| 10,009,554 | B1* | 6/2018 | Miao ........................ H04N 5/33 |
| 10,282,857 | B1* | 5/2019 | Brailovskiy .............. G06T 7/55 |
| 10,401,158 | B2* | 9/2019 | Gernoth ............. G06K 9/00221 |
| 10,521,920 | B2* | 12/2019 | Grunnet-Jepsen ... H04N 13/128 |
| 2008/0137105 | A1* | 6/2008 | Howard ............. G01N 29/2418 356/630 |
| 2011/0205341 | A1* | 8/2011 | Wilson .................... G06F 3/011 348/51 |
| 2011/0268322 | A1* | 11/2011 | Clausen ................. G01B 11/25 382/106 |
| 2011/0317005 | A1* | 12/2011 | Atkinson .................. H04N 5/33 348/135 |
| 2012/0061993 | A1 | 3/2012 | Hasegawa et al. |
| 2014/0210794 | A1* | 7/2014 | Ilmonen ................ G06F 3/0425 345/175 |
| 2014/0233796 | A1* | 8/2014 | Tanaka et al. ................ 382/103 |
| 2015/0009335 | A1* | 1/2015 | Strandemar ........... G01J 5/0025 348/164 |
| 2015/0077399 | A1* | 3/2015 | Nishioka ................ G02B 30/56 345/175 |
| 2015/0077520 | A1* | 3/2015 | Ohba ....................... G06F 3/017 348/47 |
| 2015/0136981 | A1* | 5/2015 | Kester .................. G01J 3/0229 250/330 |
| 2015/0161762 | A1* | 6/2015 | Fujiwara ................. G06T 11/60 345/633 |
| 2015/0201176 | A1* | 7/2015 | Graziosi .............. H04N 13/243 348/43 |
| 2015/0234454 | A1* | 8/2015 | Kurz .................... G06T 19/006 345/156 |
| 2015/0269742 | A1* | 9/2015 | Bergstrom ......... H04N 5/23229 348/164 |
| 2016/0004920 | A1* | 1/2016 | Armstrong-Crews ...................... G03B 35/00 348/46 |
| 2016/0231866 | A1* | 8/2016 | Tretter ....................... G06F 3/14 |
| 2016/0261300 | A1* | 9/2016 | Fei ........................... G06F 3/017 |
| 2017/0052070 | A1* | 2/2017 | Marsh .................... G01N 25/72 |
| 2017/0054966 | A1* | 2/2017 | Zhou .................... H04N 13/257 |
| 2017/0070731 | A1* | 3/2017 | Darling .................... G06T 7/85 |
| 2017/0077764 | A1* | 3/2017 | Bell ......................... H02J 7/027 |
| 2017/0212066 | A1* | 7/2017 | Thompson ........... H04N 5/2256 |
| 2017/0243372 | A1* | 8/2017 | Iida .......................... G06T 7/13 |
| 2017/0275023 | A1* | 9/2017 | Harris .................. B64C 39/024 |
| 2017/0374333 | A1* | 12/2017 | Ashra ................... H04N 9/3182 |
| 2018/0188020 | A1* | 7/2018 | Fuchikami .............. G09G 5/37 |
| 2018/0189957 | A1* | 7/2018 | Sanchez Bermudez .................... G06T 7/97 |
| 2018/0218200 | A1* | 8/2018 | Wolf ..................... G06K 9/2018 |
| 2018/0288390 | A1* | 10/2018 | Luo ...................... H04N 13/296 |
| 2018/0372481 | A1* | 12/2018 | Stigwall ............. G01B 11/2504 |
| 2019/0000564 | A1* | 1/2019 | Navab ..................... A61B 6/03 |
| 2019/0121427 | A1* | 4/2019 | Qin ........................ G06F 3/013 |
| 2019/0230303 | A1* | 7/2019 | Wang .................. G06K 9/3233 |
| 2019/0236806 | A1* | 8/2019 | Jiang ....................... G06T 7/80 |
| 2019/0325586 | A1* | 10/2019 | Zhang ...................... G06T 7/73 |
| 2019/0383730 | A1* | 12/2019 | Chang Chien ..... G01N 33/0098 |

OTHER PUBLICATIONS

MJ Services (GB) Ltd., "ThermBright Thermal Targets vs Conventional Thermal Targets", Brochure, pp. 1-2, http://www.thermbright.com/thermal-targets/benefits-a-comparison, 2010 Wiltshire, UK.

J.Rangel et al., "3D Thermal Imaging: Fusion of Thermography and Depth Cameras", Paper, Proceedings of the 2014 International Conference on Quantitative Infrared Thermography. Jan. 1, 2014 pp. 2-6. XP55439844, DOI: 10.21611/qirt.2014.035, DE.

Quellet et al., "Precise ellipse estimation without contour point extraction", Paper, Machine vision and applications, vol. 21, No. 1, May 7, 2008, pp. 59-67, XP019755540, ISSN: 1432-1769,Springer, Berlin, DE.

Jaramillo et aL, "6-DoF pose localization in 3D point-cloud dense maps using a monocular camera", Paper, 2013 IEEE International conference on Robotics and Biomimetics (ROBIO), IEEE, Dec. 2013, pp. 1747-1752, Shenzhen, CN.

Ababsa et al., "Robust Camera Pose Estimation Using 2D Fiducials Tracking for Real-Time Augmented Reality Systems", Paper, Virtual reality continuum and its applications proceedings of the 2004 ACM Siggraph International Conference on virtual Reality Continuum and its Applications in Industry, Jan. 1, 2004, pp. 1-4, XP055290191, France.

European Patent Office, Search Report and Written Opinion for corresponding PCT/EP2017/072360. dated Feb. 19, 2018. pages 1-19.

* cited by examiner

DETERMINING THE RELATIVE POSITION BETWEEN A THERMAL CAMERA AND A 3D CAMERA USING A HYBRID PHANTOM

RELATED APPLICATION DATA

This application is a National Phase Application of International Application No. PCT/EP2017/072360 filed Sep. 6, 2017 and published in the English language, which claims priority to International Application No PCT/EP2017/062384 filed on May 23, 2017, the entire contents of which are incorporated herein by reference.

TECHNICAL FIELD

The present invention relates to a method for determining the relative position between a thermal camera and a 3D camera using a hybrid phantom, to a corresponding computer program and a system.

SUMMARY

There are scenarios in medical applications in which two different cameras are used. The first camera is a thermal camera. A thermal camera senses thermal energy and outputs a thermal image. The thermal image typically is a grayscale image or a false color image and consists of a multitude of pixels, wherein the color or gray value of each pixel of the thermal image corresponds to the thermal energy of the radiation imaged by said pixel. The thermal image is for example a 2D image. The second camera, such as a Time-of-Flight (ToF) or a structured light camera, generates a 3D point cloud by emitting light onto an object and analyzing the reflected light.

It might then be necessary to know or determine the calibration between the two cameras. The calibration means the relative position between the two cameras and is also referred to as a set of extrinsic parameters. Contrary to that, intrinsic parameters of a camera describe how incoming radiation, such as light, is processed, for example using an optical system or a wave guide system, and converted into an electrical output signal. The intrinsic parameters for example describe the focal length and aberrations introduced by a camera.

In this document, the term "position" means a combination of an orientation given in up to three rotational dimensions and/or a location given in up to three translational dimensions.

In the present invention, the relative position between the cameras is determined by imaging a hybrid phantom using both cameras and analyzing the output data of the two cameras. In this document, the hybrid phantom is also simply referred to as phantom. The phantom has particular properties such that markers being part of the phantom can be recognized both in the output image of the thermal camera and in the 3D point cloud output by the second camera.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a use of a hybrid phantom for determining the relative position between a first camera and a second camera, wherein the first camera is a thermal camera which captures a thermal image of the hybrid phantom, the second camera emits light onto the hybrid phantom and analyzes the reflected light, thus generating a 3D point cloud representing points on the surface of the hybrid phantom.

The second camera is, for example, a Time-of-Flight (ToF) camera or a structured light camera. A ToF camera measures the time required by a light signal to travel to the phantom and back to the camera. In this document, the expression ToF camera comprises any suitable LiDAR apparatus. A structured light camera projects known light patterns onto the phantom and analyzes the reflected light to create the 3D point cloud.

The hybrid phantom has a planar surface comprising a background surface and a plurality of marker surfaces, wherein the background surface has one of a first property and a second property, each marker surface has the other one of the first property and the second property, the first property involves having a high thermal emissivity of 0.8 or higher and the second property involves having a low thermal emissivity of 0.2 or less. The pixels of the thermal image which show the surface with the high thermal emissivity indicate the real temperature of the surface, or at least basically the real temperature of the surface.

In one example, a high thermal emissivity is 0.9 or higher. In one example, a low thermal emissivity is 0.1 or less.

The surface with the low thermal emissivity conceals its own temperature and rather reflects incident thermal radiation to the thermal camera. So pixels of the thermal image which show the surface with the low thermal emissivity indicate the temperature of the environment of the phantom or of another object. The temperature reflected by the surface with the low thermal emissivity is referred to as ambient temperature. With this constellation, the two surfaces can be distinguished in the thermal image if the temperature of the surface with the high emissivity differs from the ambient temperature. In this document, thermal radiation means electromagnetic radiation in the thermal spectrum which is irradiated by an object.

A marker surface constitutes a marker, such that those expressions are used synonymously unless stated otherwise. The location of a marker surface, or a marker, is the location of the geometric center or the center of mass of the marker surface. Each marker surface has a boundary at which it ends and the background surface begins.

One of the first property and the second property further involves being diffuse reflective for the light emitted by the second camera, thus reflecting light emitted by the second camera back to the second camera. Diffuse reflection means that incoming radiation is reflected at more than one angle, unlike specular reflection, in which incident radiation is reflected at a single angle which is symmetrical to the incident angle with respect to the surface normal. This means that the second camera can capture the light reflected by the phantom for any orientation, or at least a range of orientations, of the phantom relative to the second camera. The second camera can then determine points on the diffuse reflective surface.

The other one of the first property and the second property involves, for example, being non-reflective or non-diffuse reflective for the light emitted by the second camera.

In this document, a surface is considered to be reflective if it reflects a certain amount of the incident light energy, such as at least 20%, 25%, 30%, 50%, 75% or 90%. A surface is considered to be non-reflective if the amount of reflected light energy is below a predetermined threshold, such as 15%, 10%, 5%, 3%, 2% or 1%. A non-reflective surface can for example absorb (most of) the incident light. A non-diffuse reflective surface can be a non-reflective surface or a specular reflective surface. A specular reflective surface does not reflect light emitted by the second camera back to the second camera for almost all positions of the phantom relative to the second camera except for a very small range of relative positions, and those relative positions can be avoided when the phantom is used for determining the relative position between the first camera and the second camera.

The property of a surface, that is reflective or not, preferably only applies to the wavelengths used by the second camera to generate the 3D point cloud. This means that a non-reflective surface is allowed to reflect non-used wavelengths back to the second camera and a reflective surface is allowed to not reflect non-used wavelengths back to the second camera.

The phantom can also have more than one planar surface, wherein two or more planar surfaces can form the background surface. Besides the one or more planar surface(s), the phantom can have additional surfaces. A surface is considered to be planar if all points on the surface have a distance to a plane fitted through those points being below a predetermined threshold, such as an absolute threshold or a relative threshold. The absolute threshold can be, for example, 10 mm, 5 mm, 3 mm, 2 mm or 1 mm. The relative threshold can for example be a fraction of the square root of the area occupied by the surface points, such as $1/10$, $1/20$, $1/50$, $1/75$, $1/100$, $1/200$ or $1/250$.

With the phantom described above, the markers have sharp contours both in the thermal image and in the 3D point cloud. In the thermal image, the surface having the first property has its real temperature, while the surface having the second property has the ambient temperature. There is a high contrast in the thermal image for example if the phantom, the surface having the first property or at least the part of the surface having the first property which is neighboring the surface with the second property is heated or cooled. The 3D point cloud comprises points on the diffuse reflective surface, but points on a non-diffuse reflective surface are either not comprised in the 3D point cloud or have assigned an infinite distance to the second camera.

In one embodiment, the phantom further comprises a plurality of x-ray markers. An x-ray marker is visible in an x-ray image of the phantom. The x-ray markers are in known positions relative to the marker surfaces, such that the position of the x-ray imaging apparatus used for capturing the x-ray image can be determined relative to the first camera and/or the second camera. The x-ray markers can for example be metallic discs, which appear as ellipse in the x-ray image.

The present invention further relates to a method for determining the relative position between a first camera and a second camera used in a medical application. The first camera is a thermal camera which captures a thermal image of a hybrid phantom. The second camera emits light onto the hybrid phantom and analyzes the reflected light, thus generating a 3D point cloud representing points on the surface of the phantom. Details of the first camera, the second camera and the hybrid phantom are the same as described above.

The method of the present invention comprises the step of capturing a thermal image of the phantom using the first camera. It further comprises the step of capturing a 3D point cloud of the phantom using the second camera. The 3D point cloud represents points at least on the planar surface of the phantom, either on the background surface or the marker surfaces.

The method further involves the step of identifying an edge of each of the plurality of marker surfaces in the thermal image, and for example a plurality of edges of each of the marker surfaces. The structure of the phantom causes a temperature difference between the background surface and the marker surfaces as imaged in the thermal image, which can be identified as edges in the thermal image.

The method further involves the step of identifying the locations of the plurality of marker surfaces from the identified edges, thus generating thermal marker locations. The thermal marker locations are preferably defined by two coordinates in the thermal image.

The present method further involves the step of identifying the locations of the plurality of marker surfaces from the 3D point cloud, thus generating 3D marker locations. This identification uses the property that points on a non-diffuse reflective part of the planar surface are identified as having a larger distance to the second camera than points on a diffuse reflective part of the planar surface. If a particular point on a non-diffuse reflective part does not reflect light back to the second camera, the distance of this point to the second camera is found to be large or even infinite. With the diffuse reflective/non-diffuse reflective properties of the marker surfaces and the background surface as explained above, the shapes of the markers can also be identified in the 3D point cloud. Identifying the locations of the markers from the 3D point cloud thus obtains 3D marker locations of the markers in a reference system of the second camera. The locations of the markers for example represent the centers, such as the centers of mass, of the marker surfaces in space.

The present method further involves the step of determining the relative position between the first camera and the second camera from the thermal marker locations and the 3D marker locations. This can be done using any algorithm which finds a relative position between the cameras such that the 3D marker locations would be depicted in the thermal image at the thermal marker locations.

In one implementation, the relative position between the first camera and the second camera is determined by applying a Perspective-n-Points (PnP) algorithm on the thermal marker locations and the 3D marker locations.

The Perspective-n-Points algorithm finds a virtual position of the first camera relative to the second camera for which the markers at the 3D marker locations would result in locations of the markers in the thermal image of the first camera as represented by the thermal marker locations. Put differently, the location of a marker in the thermal image in combination with the intrinsic parameters of the first camera defines a line in space, relative to the first camera, on which the marker must lie. Any point on this line is imaged at the corresponding location in the thermal image due to the properties of the first camera. Now a relative position between the cameras has to be found such that the 3D marker locations lie on the lines in space corresponding to the thermal marker locations.

Given a set of 3D points (3 or more) and their corresponding 2D points and the camera matrix (K) of the thermal camera which is used for imaging the 2D points, the Perspective-n-Points algorithm determines the rotation (R) and translation (T) needed in the projection formula of the pin camera model:

$$sp_{2d}=K[R|T]p_{3d}$$

Where all the vectors and matrices are in their homogeneous form (this means with an added dimension having the value of 1 for the vectors, and a row of 0 and 1 for the matrix, wherein the 1 will go in the diagonal position). The camera matrix represents the intrinsic parameters used in the pinhole camera model. It has the focal length of the camera in pixels and the optical center in pixels as well. The camera matrix is parameterized as follows:

$$K = \begin{pmatrix} f_x & sk & x_0 \\ 0 & f_y & y_0 \\ 0 & 0 & 1 \end{pmatrix}$$

In this matrix, $f_x$ and $f_y$ are focal lengths, sk is the axis skew and $x_0$ and $y_0$ represent the principal point offset. Then s is the resulting scale, since the result will be of the form:

$$p_{2d} = \begin{bmatrix} x \\ y \\ w \end{bmatrix}$$

$$s = \frac{1}{w}$$

And to be homogeneous, w should be equal to 1.

There are several solutions to find the extrinsic parameters ([R|T]) with the Perspective-n-Points algorithms. However, all the variants use the same inputs and will output the Extrinsic parameters (in some cases, an optimized camera matrix as well).

As an example, P3P uses only 3 points to create a system of equations, which will give 4 solutions, and then uses a 4th point to obtain a single solution and discard the rest.

EPnP uses at least 3 points (more points will yield better results in case the data is noisy), to generate several equations based on the sum of 4 weighted control points equal to the data points (4 for the 3D data and 4 for the 2D data), this equations are used to calculate the coefficients needed for the direct calculation of the extrinsic parameters.

In a final example, a system of equations is built out of the equation given before with all the points. Then, using a random or educated guess, it is then refine in an iterative way using gauss newton minimization (minimizing the re-projection error) or Levenberg Marquadt (minimizing the re-projection error as well).

In one embodiment, identifying an edge of a marker surface and identifying the location of a marker surfaces involve finding two or more edge pixels lying on the boundary of a marker surface, calculating a direction of a gradient for each found edge pixel and calculating the location of the marker surface from the directions of the gradient. Due to the imaged temperature difference at the boundary of the marker surface, there is a significant color change in the false color thermal image and a significant change in the gray value in a gray scale thermal image. An edge pixel is found, for example, by finding such a significant difference in neighboring pixels of the thermal image. At each edge pixel, the thermal image has a gradient, and the direction of the strongest gradient is particularly perpendicular to the boundary of the marker surface. The direction of the gradient means the direction of the largest gradient of the edge pixel. Calculating the location of the marker surface from the directions of the gradients for example involves analyzing the intersections of straight lines running through the edge pixels and having the directions of the corresponding gradients. Details of this approach are described in the article "Precise ellipse estimation without contour point extraction" published in the Journal Machine Vision and Applications, Volume 21 Issue 1, October 2009, Pages 59-67.

In another embodiment, the location of a marker is identified, for example, based on the known shape of the marker surface. The shape of the marker surface, or of its projection into the image plane of the thermal image, is identified in the thermal image. For example, a plurality of edge pixels lying on the boundary of the marker surface are identified and an object having the shape corresponding to the shape of the marker surface is fitted into the edge pixels. If the marker surface is, for example, circular, the depiction of the marker surface in the thermal image is elliptical, and an ellipse is fitted into the edge pixels. A suitable algorithm for finding ellipses, which correspond to depictions of circular markers, in the thermal image is described in the paper "Precise ellipse estimation without contour point extraction" by Ouellet et al. The center of the fitted object then defines the thermal marker location.

In one embodiment, the method further involves rotating the 3D point cloud such that the planar surface of the phantom, as represented by the rotated 3D point cloud, is perpendicular to the depth direction of the reference system of the second camera, thus obtaining a 2D view of the 3D point cloud. The depth direction is typically the z axis in the reference system of the second camera. In this context, the expression "2D view" means that all points in the 3D point cloud corresponding to the diffuse reflective part of the planar surface of the phantom have the same depth to the second camera. The 2D view therefore does not comprise spatial deformations caused by the viewing direction of the second camera onto the phantom.

In this embodiment, the method further involves the steps of identifying the locations of the markers in the 2D view, thus obtaining auxiliary marker surface locations, and of performing an inverse rotation of the auxiliary marker surface locations, thus obtaining the 3D marker locations. In the 2D view, the shape of a marker equals the actual physical shape of the marker surface of the phantom. It is thus easier to find the markers in the 2D view. The inverse rotation is the inverse of the rotation applied to the 3D point cloud to obtain the 2D view. The found locations of the markers in the 2D view are thus transformed back into 3D space, thus forming the locations of the marker surfaces in the reference system of the second camera.

In one implementation of this embodiment, a plane is fitted into those points of the 3D point cloud which represent the planar surface of the phantom. Then a transformation is calculated which describes rotations about axes perpendicular to the depth direction of the reference system of the second camera and which makes the plane perpendicular to the depth direction of the reference system of the second camera. This transformation is then applied to the 3D point cloud to obtain the 2D view and the inverse of the transformation is applied to the auxiliary marker surface locations, thus obtaining the 3D marker locations. In one example, the points of the 3D point cloud which represent the planar surface of the phantom are points on the diffuse reflective surface.

In one implementation, the method according to this embodiment involves the step of removing, from the 3D point cloud, those points which do not lie on the plane. This step can be performed before or after the 3D point cloud is rotated. A point is considered as lying on the plane if its distance to the plane is below a threshold, such as the absolute threshold or relative threshold mentioned above in the definition of the word "planar". With this step, the 3D point cloud is basically reduced to points lying on the planar surface.

In one implementation of this embodiment, the 2D view is a depth map of the rotated 3D point cloud. A depth map is a (virtual) 2D image in which the color of each pixel, or the grey value in a grey scale image, represents the distance of a surface point depicted by this pixel from the second camera. In this implementation, points on a diffuse reflective surface basically have the same color/grey value in the 2D view and points on a non-diffuse reflective surface have a significantly different color/grey value.

In one embodiment, a deviation value of the relative position between the first camera and the second camera is calculated and the steps of capturing a thermal image of the phantom, identifying an edge of each of the plurality of marker surfaces in the thermal image, identifying the locations of the plurality of marker surfaces from the identified edges, thus generating thermal marker locations, capturing a 3D point cloud of the phantom, identifying the locations of the plurality of marker surfaces from the 3D point cloud, thus generating 3D marker locations, and determining the relative position between the first camera and the second camera from the thermal marker locations and the 3D marker locations are repeated if the deviation value is above a predetermined threshold. With this approach, the confidence of the determined relative position is judged and the process is repeated if this confidence is not high enough.

In one implementation of this embodiment, the 3D marker locations are projected into the image plane of the first camera using the determined relative position between the two cameras and intrinsic parameters of the first camera. In other words, it is simulated at which locations the marker surfaces would be in the thermal image, considering the found relative position and the imaging properties of the first camera. Then the distances between the locations of the markers of the projected 3D marker locations in the image plane and the locations of the corresponding markers found in the thermal image are calculated and the deviation value is calculated from said distances. In other words, the real locations of the markers in the thermal image are compared to the simulated locations. If the deviation value is above a predetermined threshold, the confidence is not high enough.

In one implementation, the deviation value is the root mean square of the distances, but any other suitable metric can be used.

In one embodiment, the method further involves the step of establishing a one-to-one correspondence between the markers represented by the thermal marker locations and the 3D marker locations. This facilitates the calculation of the deviation value.

One possible implementation asks for user input which identifies corresponding markers, for example in the thermal image and the 3D point cloud or in the thermal image and the 2D view of the 3D point cloud. The correspondence can also be established automatically. In one example, each marker comprises a unique identification which can be identified both in the thermal image and the 3D point cloud (or the 2D view of the 3D point cloud). The identification can be, for example, any one of a number, a shape or any other code.

In another implementation, the markers in both the thermal image and the 2D view of the 3D point cloud are ordered in a particular order, such as from left to right and from top to bottom. Since the planar surface must be visible to both cameras, the viewing directions of those cameras onto the planar surface are on the same side of the planar surface. The left-to-right arrangement of the markers in the thermal image and in the 2D view of the 3D point cloud is therefore identical. It is therefore only possible that the up-down directions of the thermal image and the 2D view of the 3D point cloud are inversed. However, this can typically be disambiguated automatically from the arrangement of the markers.

Another implementation can use prior knowledge about the positions of the markers on the planar surface. This prior knowledge does not have to reflect the exact positions, but only the general arrangement of the markers. In this prior knowledge, every marker can have a unique identification.

In one embodiment, the method further involves the step of adjusting the temperature of at least a part of the background surface of the hybrid phantom such that it differs from the ambient temperature. This increases the temperature difference at the boundary of the marker surfaces in the thermal image.

In one implementation, the hybrid phantom is cooled using a cooling element. This can be a cooling element attached to or being a part of the phantom, such as a Peltier element or an air-conditioning compressor. The cooling element can be a volume within the phantom, wherein the volume is filled with a cool substance or the cool substance flows through the volume. In general, any means which generate cold can be used, such as a device in which a compressed gas or liquid is expanded or an endothermic reaction occurs. The cooling element can also be a cooled environment, such as a refrigerator, which pre-cools the phantom before it is used for determining the relative position between the cameras.

In another implementation, the hybrid phantom is heated using a heating element. The heating element can be attached to or be a part of the hybrid phantom and can for example be a resistance-heating device, an element which is filled with a hot substance or through which a hot substance flows or an element in which an exothermic reaction occurs. The heating element can further be a radiating device which radiates thermal energy corresponding to a temperature higher than the ambient temperature onto the phantom. Examples of such a radiating device are a red light lamp or a resistance heating device. The heating element can further be an element which heats the environment of the hybrid phantom, such as an oven. The heating element can further be an element which pre-heats the phantom. such as a heat delivering docking station or a heating pack. The heating element can further be the hot side of a Peltier element or an air-conditioning compressor. The heating element can further be a microwave radiation source which emits electromagnetic microwave radiation onto the phantom which then heats the phantom.

The temperature of the hybrid phantom can be adjusted prior to using the phantom for determining the relative position between the first camera and the second camera, but can also be adjusted during use.

In one implementation, the hybrid phantom comprises metallic inlays forming the plurality of marker surfaces and the metallic inlays are heated such that the heat dissipates into the background surface surrounding the marker surfaces. The heat dissipating into the background surface forms a thermal halo around the marker surface. The surfaces of the metallic inlays which form the marker surfaces are preferably polished to achieve a low thermal emissivity.

The metallic inlays can be pre-heated before they are inserted into the hybrid phantom. They can also be heated while they are in the hybrid phantom, for example using a heating element such as a resistance-heating device.

The present invention further relates to a program which, when running on a computer, causes the computer to perform the method as explained above and/or to a program storage medium on which the program is stored, in particular in a non-transitory form.

The present invention further relates to a computer on which the aforementioned program is stored and/or run.

Still further, the present invention relates to a system comprising a hybrid phantom as defined above, a first camera, a second camera and a computer as explained above.

In one embodiment, the system further comprises heating means for heating the hybrid phantom or cooling means for cooling the hybrid phantom. Heating means and cooling means can be as described above.

In one embodiment, the hybrid phantom comprises metallic inlays forming the plurality of marker surfaces and further comprises heating means for heating the metallic inlays. As explained above, heat dissipates from the metallic inlays into the phantom, and in particular into the background surface, surrounding the metallic inlays. The background then emits thermal energy corresponding to the dissipated temperature, while the surface of the metallic inlays which form the marker surfaces reflect the ambient temperature to the first camera and thus seem cooler than the surrounding background surface.

In the present invention, the thermal marker locations and the 3D marker locations are analyzed. Since those marker data represent the same phantom, and therefore the same relative positions of the markers on the phantom, it is not necessary to know the exact arrangement of the markers on the phantom, which means that, for example, inaccuracies in the manufacture of the phantom are irrelevant.

Another advantage of the present invention is that is only requires one pair of a thermal image and a 3D point cloud. It is not necessary to capture a plurality of thermal images and/or generate a plurality of 3D point clouds, for example at different points in time or for different positions of the phantom.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks. netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google. Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer, a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The present invention can be used for the applicant's Radiotherapy and Image Guided Surgery devices where it enables a precise positioning and monitoring of patients.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
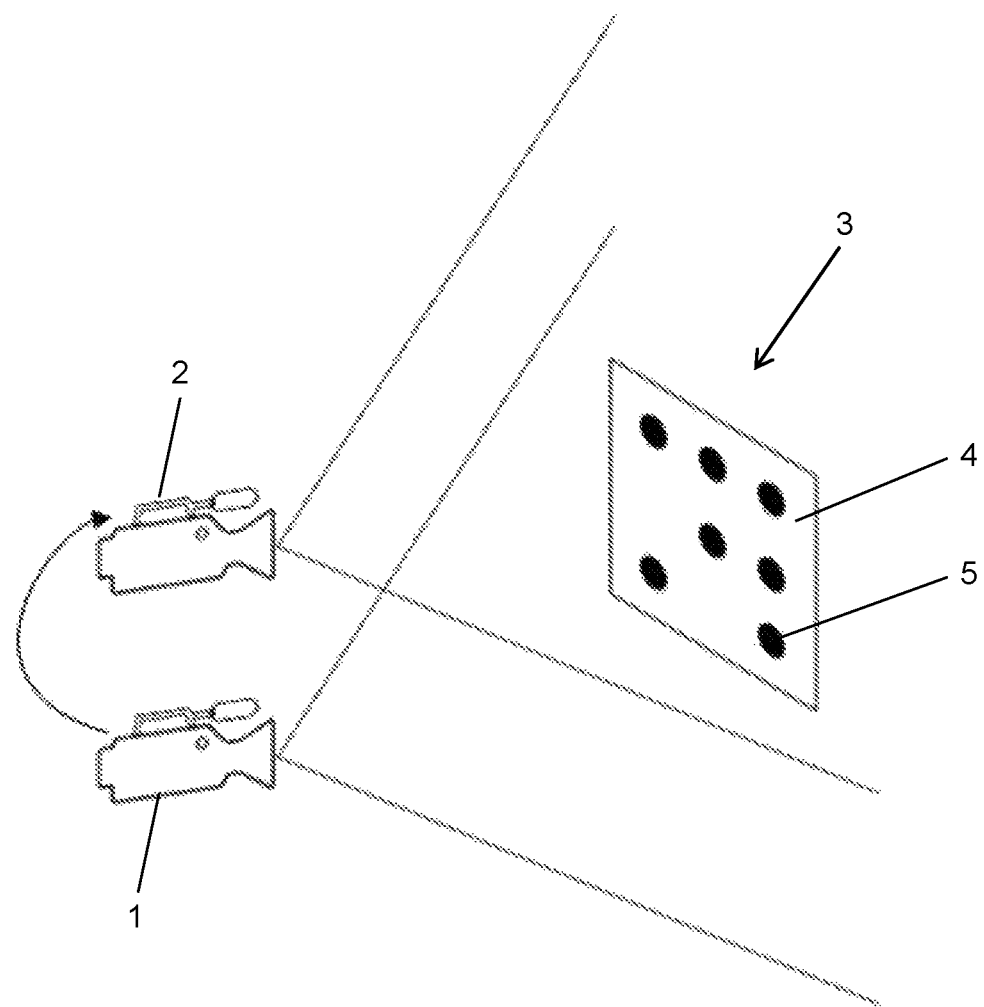
FIG. 1 a setup with two cameras and a phantom,
FIG. 2 a system according to the present invention,
FIG. 3 thermal energy detected by the first camera,
FIG. 4 a flow chart including the present invention,
FIG. 5 a detailed flow chart of analyzing the thermal image,
FIG. 6 a detailed flow chart of analyzing the 3D point cloud,
FIG. 7 a reduced and transformed version of the 3D point cloud,
FIG. 8 an exemplary hybrid phantom,
FIG. 9 another exemplary hybrid phantom, and
FIG. 10 yet another exemplary hybrid phantom.

FIG. 1 shows a setup of a first camera 1 and a second camera 2. The first camera 1 is a thermal camera which can capture a thermal 2D image of an object. The thermal 2D image is for example a grayscale image having a multitude of pixels, wherein the gray value of a pixel corresponds to the temperature of the surface of the object at a location imaged by that pixel. The second camera 2 is a structured light camera which can generate a 3D point cloud of the object by emitting a light pattern onto the object and analyzing the light reflected back to the camera.

If the output of both cameras 1 and 2 is to be used in a medical procedure, it is typically essential to know the relative position between the first camera 1 and the second camera 2. This relative position is also referred to as extrinsic parameter of the pair of cameras. It can also be understood as a transformation between the position of the first camera 1 and the second camera 2. It is indicated by the arrow in FIG. 1.

According to the present invention, the relative position between the two cameras 1 and 2 is not determined by tracking markers attached to the cameras. The relative position is rather determined by placing a hybrid phantom 3 in the field of view of both cameras and analyzing the output of the two cameras.

In general, the phantom 3 can have any shape. However, it must have a planar surface comprising a background surface 4 and a plurality of marker surfaces 5. In the present example, the background surface 4 is diffuse reflective, thus reflecting light emitted by the second camera 2 back to the second camera. The background surface further has a high thermal emissivity of 0.8 or more. The marker surfaces 5 have a low thermal emissivity of 0.2 or lower and are non-diffuse reflective, for example specular reflective. The marker surfaces 5 thus do not reflect light emitted by the second camera 2 back to the second camera 2 except for adverse relative positions between the second camera 2 and the phantom 3. However, those adverse relative positions can be avoided when the system is used. In the present example, the marker surfaces 5 are circular. However, they can have any other suitable shape.

The background surface 4 has a geometric size in terms of a surface area. The background surface 4, and therefore the planar surface, is considered to be planar if the distance of the points on the surface from a plane fitted into those points is small compared to the surface area of the planar surface, and is, for example, smaller than $1/50$ or $1/100$ of the square root of the size of the planar surface/background 4.

Figure 2:
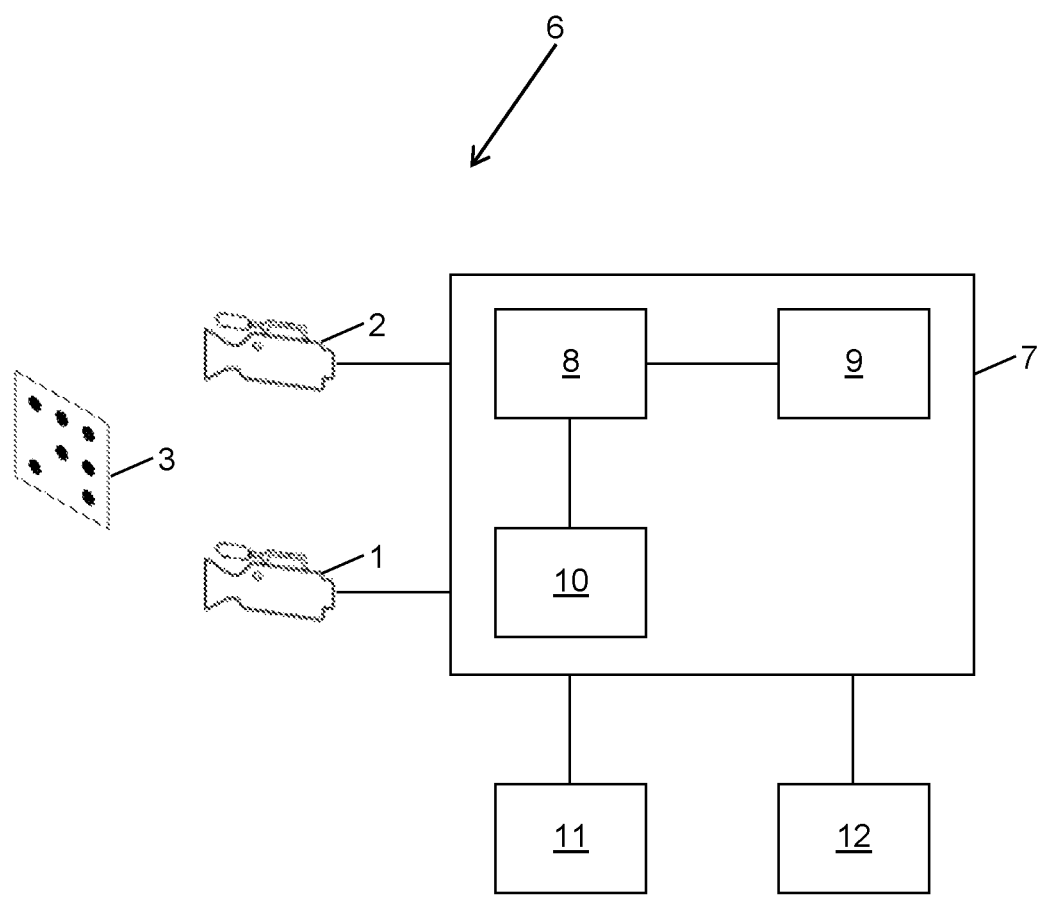

FIG. 2 shows a system 6 according to the present invention. The system 6 comprises the first camera 1, the second camera 2. the phantom 3 and a computer 7, which is connected to an optional input device 11 and an optional output device 12. The input device 11 is, for example, a keyboard, a mouse or a touch sensitive surface. The output device 12 is, for example, a monitor.

The computer 7 comprises a central processing unit (CPU) 8, a memory unit 9 and an interface 10. Via the interface 10, the computer 7 is connected to the first camera 1 and the second camera 2.

The memory unit 9 stores program data comprising instructions for the CPU 8 such that it performs the data processing according to the present invention. It further stores data to be processed, such as the thermal image captured by the first camera 1 and the 3D point cloud generated by the second camera 2, and processed data.

Figure 3:
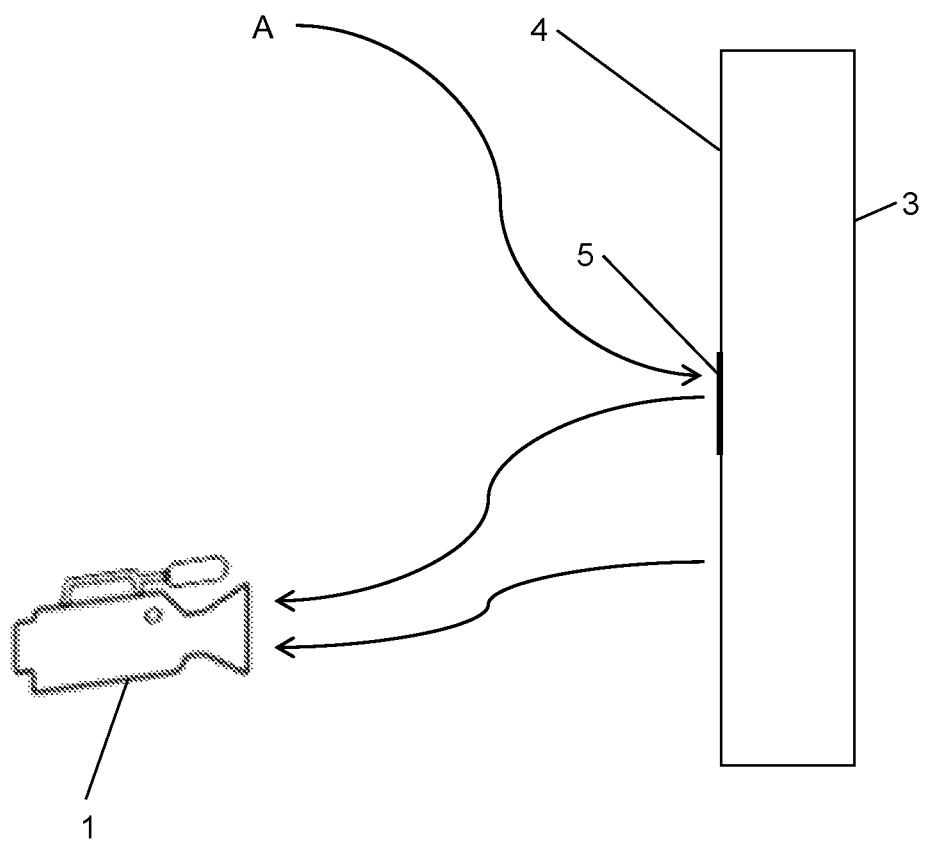

FIG. 3 shows the thermal radiation captured by the second camera 2. The hybrid phantom 3 has a particular temperature. Since the background surface 4 has a high thermal emissivity, a pixel of the thermal image corresponding to a point on the background surface basically shows the actual temperature of the phantom 3. However, the marker surfaces 5 have a low thermal emissivity, such that a pixel of the thermal image which corresponds to a point on a marker surface 5 indicates an ambient temperature A, because thermal radiation corresponding to the ambient temperature onto the marker surface 5 is reflected into the second camera 2. Since the system is typically used indoors, the thermal radiation incident onto the marker surfaces 5 and reflected into the second camera 2 originates from the floor, the ceiling or a wall of the room or an object within the room, and thus represents the temperature thereof.

Figure 4:
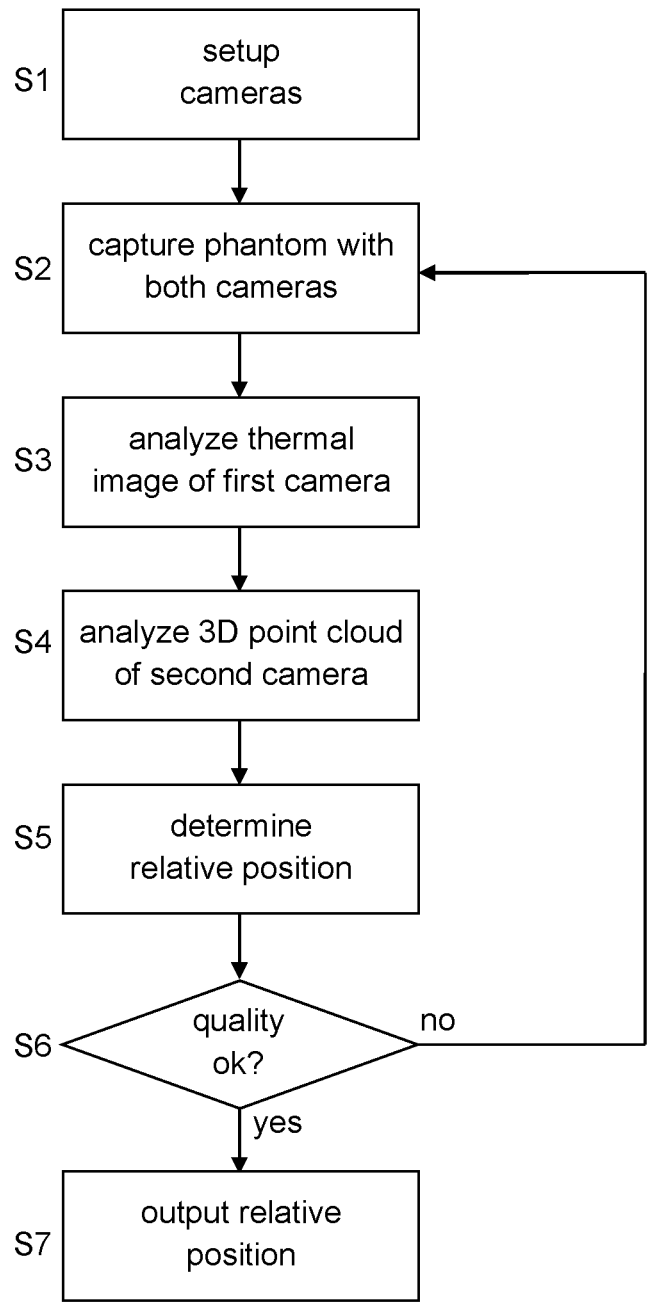

FIG. 4 shows a flowchart of a method including the present invention.

In step S1, the cameras 1 and 2 are set up. This means that the cameras are positioned as required for the medical procedure to be performed. In addition, the phantom 3 is positioned relative to the cameras 1 and 2 such that they can capture the planar surface of the phantom 3 and the marker surfaces 5 of the phantom does not reflect the light emitted by the second camera 2 back to the second camera 2. Once step S1 has been performed, the method of the present invention can be carried out.

In step S2. the phantom 3 is captured by both the first camera 1 and the second camera 2. This means that the first camera 1 captures a thermal image of the phantom 3 and the second camera 2 generates a 3D point cloud representing points on the surface of the phantom 3. In particular, a light source of the second camera 2 emits a light pattern onto the phantom 3 and analyzes the pattern of the reflected light to determine distances of points on the phantom 3. The second camera typically generates the 3D point cloud as a set of 3D coordinates in the reference system of the second camera. The 3D coordinates are typically x, y and z coordinates, wherein the z coordinate represents a depth direction of the second camera 2. The x, y and z axes constitute an orthogonal coordinate system.

In step S3, the thermal image captured by the first camera 1 is analyzed. This means that the locations of the marker surfaces 5 are identified in the thermal image. This in particular means determining the locations of the marker surfaces 5, in particular of the centers of the marker surfaces 5, in the thermal image. The locations of all identified marker surfaces 5 are then commonly referred to thermal marker locations. Due to the intrinsic parameters of the first camera 1, every location of a marker surface 5 in the thermal image has an associated line in space on which the corresponding marker surface 5 lies. This line in space is defined with respect to the first camera 1.

In step S4, the 3D point cloud generated by the second camera 2 is analyzed. This means that the marker surfaces 5 are identified in the 3D point cloud. Identifying a marker surface in the 3D point cloud means finding the location of the marker surface 5, in particular of the center of the marker surface 5, in space, defined in a reference system of the second camera 2. Step S4 results in 3D marker locations representing the locations of the found marker surfaces 5, for example in terms of a set of three-dimensional coordinates. Details of step S4 will be explained later.

In step S5, the relative position between the first camera 1 and the second camera 2 is determined. This is for example achieved by applying a Perspective-n-Points algorithm on the thermal marker locations and the 3D marker locations. The Perspective-n-Points algorithm finds a position of the first camera 1 relative to the second camera 2 such that simulated locations of the marker surfaces 5 in a simulated thermal image match the locations represented by the thermal marker locations, either exactly or as closely as possible. The simulated locations are calculated by projecting the 3D marker locations into the image plane of the first camera 1, considering an assumed relative position and the intrinsic parameters of the first camera 1.

The relative position between the cameras 1 and 2 establishes the positions of the lines corresponding to the thermal marker locations, which are originally defined relative to the first camera 1, in the reference system of the camera 2. The PnP algorithm finds a relative position such that the 3D marker locations lie on those lines. This is facilitated by the optional step of establishing a one-to-one correspondence of the markers found in the thermal image and the markers found in the 3D point cloud, which means a one-to-one correspondence between every one of the thermal marker locations with one of the 3D marker locations. It is then known which one of the 3D marker locations must lie on which line corresponding to the thermal marker locations.

In step S6, it is determined whether or not the quality of the found relative position is sufficient, which means that the deviation of the found relative position between the first camera 1 and the second camera 2 and the correct relative position is below a predetermined threshold. A suitable metric is the root mean square of the pair-wise distances between the thermal marker locations and the corresponding virtual locations explained above. The found relative position is good enough if this root mean square is below a predetermined threshold.

If the quality is not good enough, then the process returns to step S2, where the phantom 3 is captured again using both the first camera 1 and the second camera 2. Steps S3 to S5 are then repeated with the new thermal image and the new 3D point cloud.

If it is determined in step S6 that the quality is good enough, then the relative position is output in step S7, for example to a computer or a software which analyzes the output of the first camera 1 and/or the second camera 2 during a medical procedure.

Figure 5:
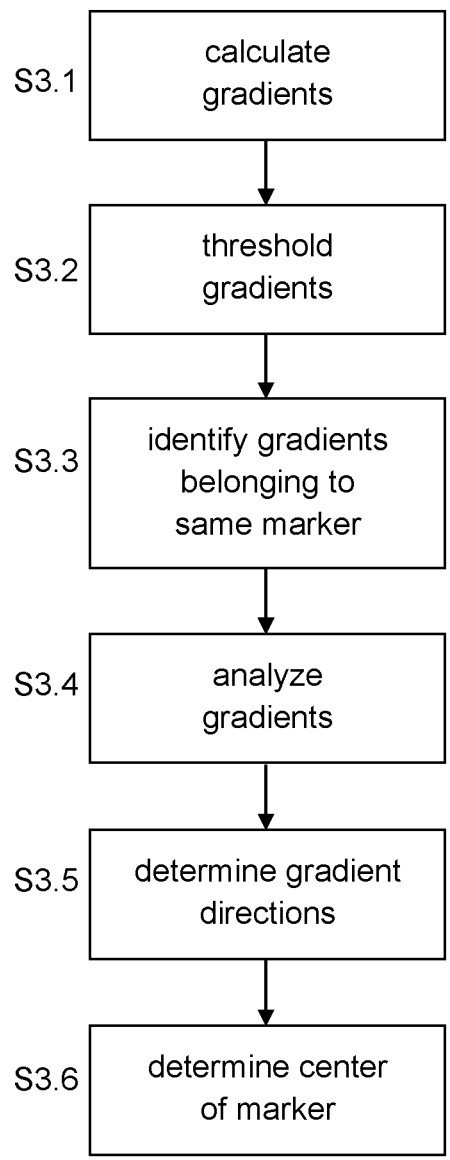

FIG. 5 shows a detailed flowchart of the step S3 of analyzing the thermal image in FIG. 4.

In step S3.1, a gradient is calculated for each one of the pixels of the thermal image. In the present example of the thermal image being a gray scale image, a current pixel, which is a pixel for which the gradient is currently being calculated, has a particular gray value. A most similar pixel among the up to eight neighboring pixels of the current pixel is identified. wherein the gray value of the most similar pixel is closest to the gray value of the current pixel among all neighboring pixels. The gradient of the current pixel is then the absolute difference between the gray values of the current pixel and the most similar pixel.

In optional step S3.2, the gradients found in step S3.1 are thresholded. This means that gradients below a predetermined threshold are discarded. As a result, only gradients indicating a minimum temperature difference are maintained.

In step S3.3, gradients belonging to the same marker surface 5 are identified. Two gradients are for example considered to belong to the same marker surface 5 if their distance in the thermal image is below a predetermined distance threshold. All gradients identified as belonging to the same marker are referred to as a set of gradients. In one implementation, the set of gradients is grown from a seed gradient until there are no more gradients within the distance threshold.

In optional step S3.4, the set of gradients is discarded if it comprises less than a predetermined number of gradients, such as 2, 5, 10 or 20 gradients. This removes sets of gradients which do not belong to an actual marker surface 5, but are rather caused by noise, or sets of gradients for which the center of the corresponding marker surface 5 cannot be reliably determined.

In step S3.5. the directions of the gradients in the set of gradients are determined. The direction of a gradient is the direction in which the gradient is the strongest, which means the direction in which the strongest change of gray values occurs.

In step S3.6, the center of a marker surface 5 corresponding to the set of gradients is determined.

Steps S3.3 to S3.6 are repeated until no more marker surfaces 5 can be identified in the thermal image and/or no more centers of marker surfaces 5 in the thermal image can be determined.

Figure 6:
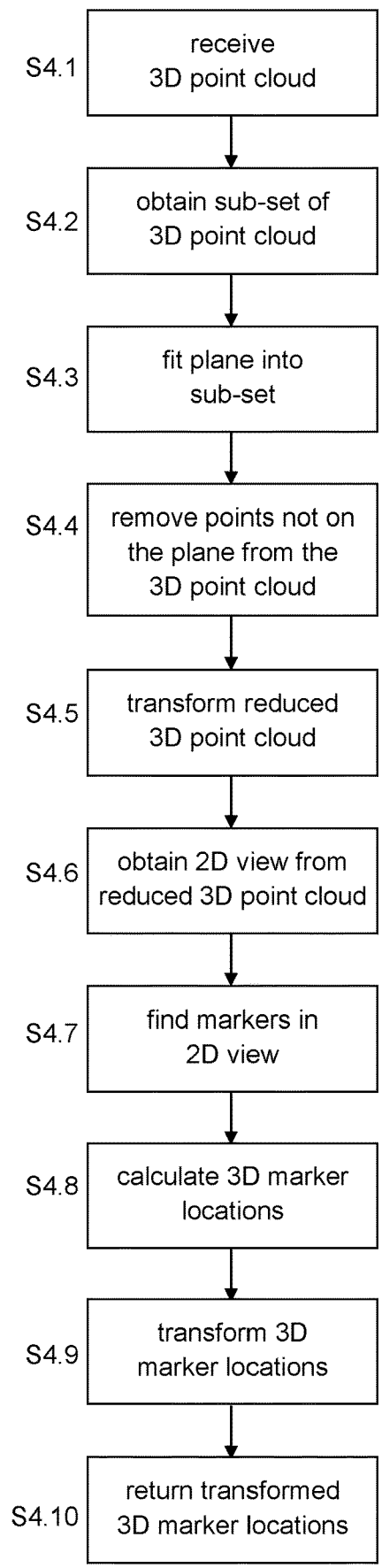

FIG. 6 shows a detailed flowchart of the step S4 of analyzing the 3D point cloud in FIG. 4.

In step S4.1, the 3D point cloud is received.

In optional step S4.2, a sub-set of the 3D point cloud is obtained. The sub-set of the 3D point cloud only comprises points lying on the planar surface of the phantom 3, which means points on the background surface 4 and/or points on the marker surfaces 5. However, it is not necessary that the sub-set contains all points on the planar surface.

One implementation of step S4.2 assumes that the phantom 3, and thus its planar surface, is placed in a predetermined location relative to the second camera 2. Points on the planar surface then lie in a predetermined range of the x and y coordinates of the reference system of the second camera 2. Points in this range then constitute the sub-set of the 3D point cloud.

It is further possible to optionally grow this sub-set by adding neighboring points of the 3D cloud which lie in the plane defined by the points within said range. A point might be considered as lying in the plane if its distance to the plane is below a predetermined threshold as explained with reference to step S4.4 below.

The background surface 4 of the phantom 3 might have a boundary around it which has the same property (diffuse reflective or non-diffuse reflective) as the marker surfaces 5. The growth of the sub-set can be stopped if this boundary is reached.

In step S4.3, a plane is fitted into the 3D point cloud or, if applicable, the sub-set of the 3D point cloud obtained in step S4.2. In addition, the orientation of a normal to the found plane is calculated. Any suitable algorithm for fitting a plane into a set of points can be used.

In step S4.4. points which do not lie in the plane are removed from the original 3D point cloud. It shall be noted that not only points which lie exactly in the plane are maintained in the 3D point cloud, but also points with a distance to the plane which is below a certain threshold. This threshold can be an absolute threshold, such as 1 mm, 2 mm, 3 mm, 4 mm or 5 mm. The threshold can also be a relative threshold which is defined in relation to the size of the planar surface, for example the square root of the size of the planar surface. The result of step S4.4 is a reduced 3D point cloud.

In step S4.5, the reduced 3D point cloud is transformed, in particular rotated. In particular, the reduced 3D point cloud is transformed such that the normal to the plane found in step S4.3 is parallel to the z-axis of the reference system of the second camera 2. In the case of a structured light camera as the second camera 2. the x- and y-axes of the camera's reference system lie in the image plane of the structured light camera and the z-axis is perpendicular thereto. With the transformation performed in step S4.5, all points in the reduced 3D point cloud have basically or exactly the same distance to the second camera 2.

Figure 7:
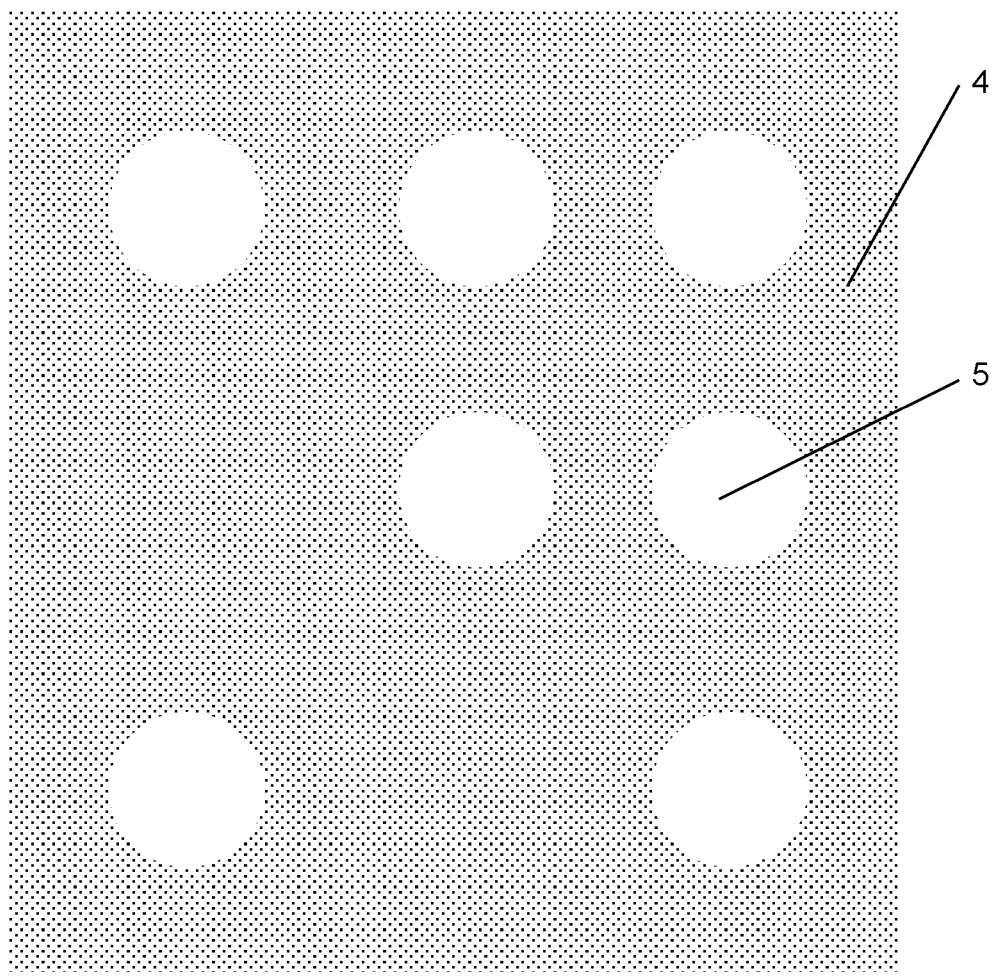

FIG. 7 shows an example of a reduced and transformed 3D point cloud. There are only points corresponding to the background surface 4 of the planar surface. At the locations of the marker surfaces 5, there are no points in the reduced and transformed version of the 3D point cloud because the marker surfaces 5 have not reflected light back to the second camera 2.

In step S4.6, a 2D view is obtained from the reduced and transformed 3D point cloud. The 2D view is. for example, a 2D grey-scale image, wherein the grey value of a pixel is determined from one or more corresponding points in the reduced and transformed 3D point cloud. This means mapping the 3D coordinates of the points in the reduced and transformed 3D point cloud into 2D coordinates in the 2D view and a grey value.

Since all points of the reduced and transformed 3D point cloud have (basically) the same distance to the second camera 2, the corresponding pixels in the 2D view have the same or almost the same grey value. However, pixels corresponding to the marker surfaces 5 are either black or white, depending on the mapping of the distance to the grey values. The 2D view can also be binarized, such that pixels corresponding to the background surface 4 are white and pixels corresponding to the marker surfaces 5 are black, or vice versa.

The markers are then identified in the 2D view in step S4.7. The same algorithm as in step S3 can be used. The results of step S4.7 are the locations of the markers, in particular of the centers of the markers, in the image plane of the 2D view.

In step S4.8, the locations of the markers found in step S4.7 are transformed into 3D marker locations. This involves an inverse mapping to the mapping performed in step S4.6. In particular, the 2D coordinate of a location is mapped to the x and y coordinates in the reference system of the second camera. The z coordinate for example corresponds to the z coordinate of one of the points in the reduced and transformed 3D point cloud or the average of the z coordinates of two or more points in the reduced and transformed 3D point cloud.

The 3D marker locations resulting from step S4.8 represent the centers of the "holes" in the reduced and transformed 3D point cloud. In step S4.9, those 3D marker locations are transformed using the inverse of the transform used in step S4.5. This means that the 3D marker locations are transformed to the original position of the 3D point cloud relative to the second camera 2. In step S4.10, the transformed 3D marker positions are returned as the 3D marker locations.

Figure 8:
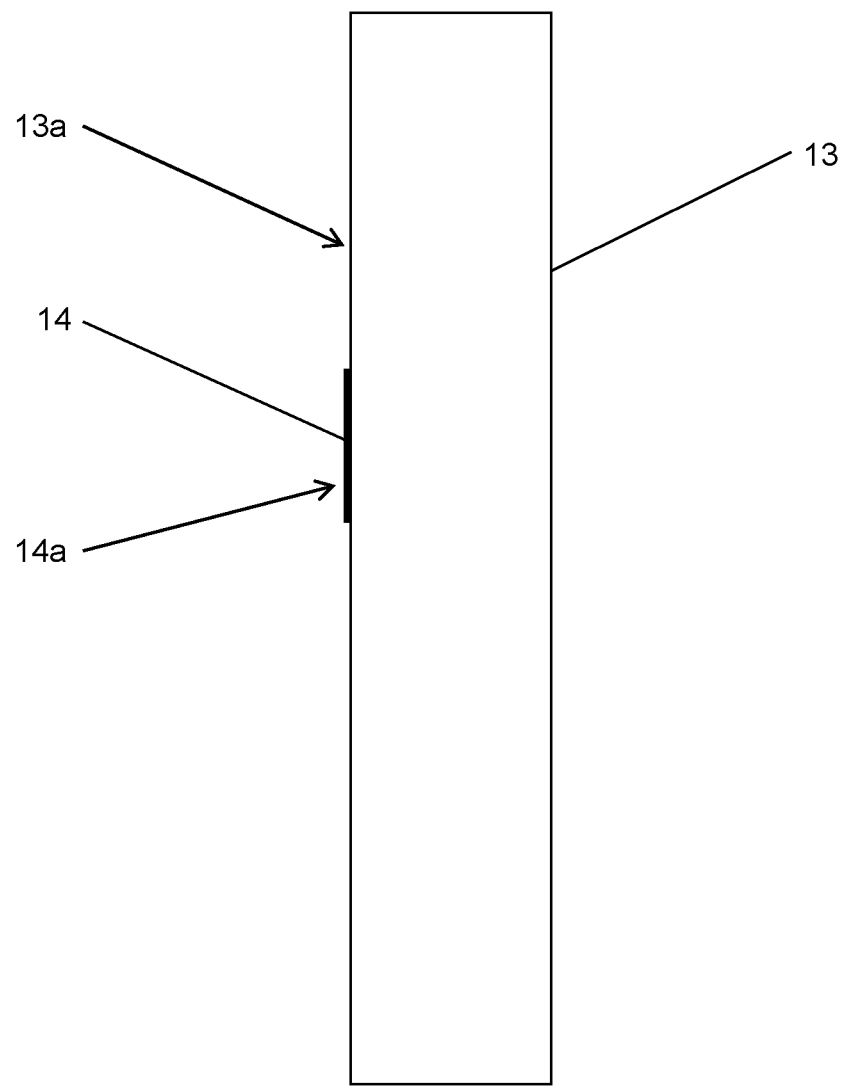

FIG. 8 schematically shows an exemplary hybrid phantom. The phantom comprises a phantom body 13 forming a background surface 13a having a high thermal emissivity.

Formed on the phantom body 13 are metal foils 14, such as an aluminum foils, having marker surfaces 14a. In FIG. 8, only one of the metal foils is shown. The background surface 13a is diffuse reflective and for example white to reflect a large amount of incident light emitted by the second camera 2. The marker surfaces 14a of the metal foils 14 are polished and thus both specular reflective and have a low thermal emissivity.

Figure 9:
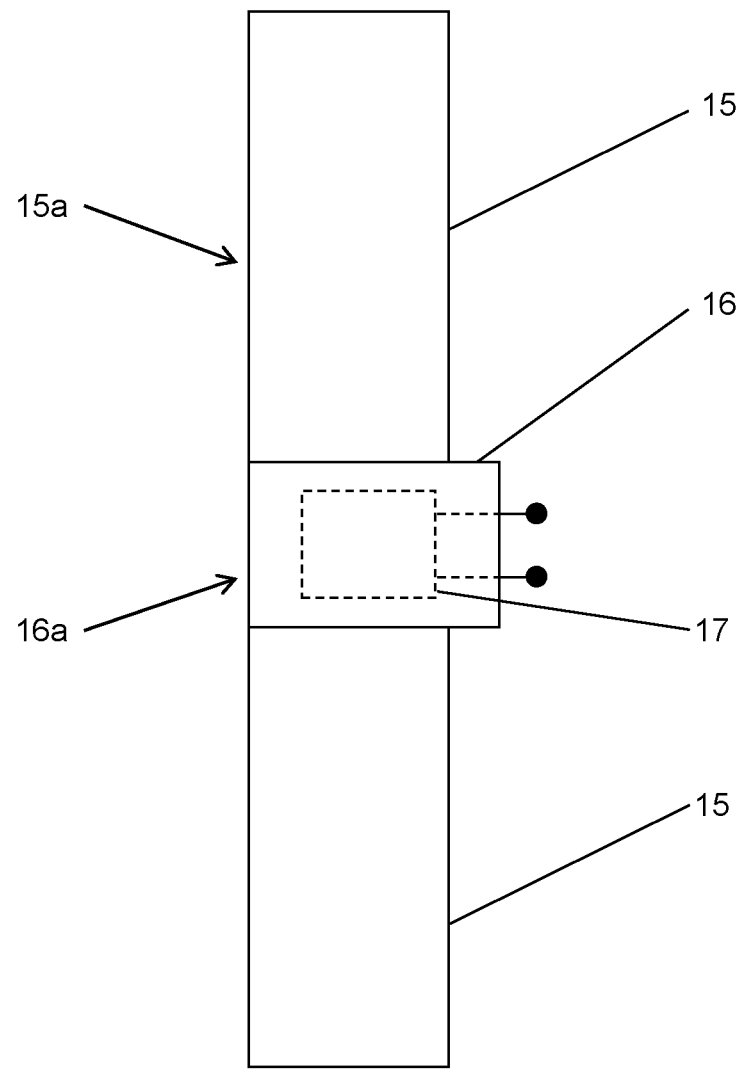

FIG. 9 schematically shows another exemplary hybrid marker comprising a marker body 15 and an exemplary metallic inlay 16. The marker body 15 forms a background surface 15a having a high thermal emissivity and being diffuse reflective for the light of the second camera 2. The metallic inlay 16 forms a marker surface 16a which is polished and therefore has a low thermal emissivity. In addition, the marker surface 16a is specular reflective for the light of the second camera 2. Only one of multiple metallic inlays 16 is shown in FIG. 9.

The metallic inlay 16 comprises a heating element 17 in terms of a resistance-heating element. If electricity is applied to the heating element 17, it heals up the metallic inlay 16. The thermal energy originating from the heating element 17 then dissipates into the phantom body 15 surrounding the metallic inlay 16. At least the part of the background surface 15a which surrounds the metallic inlay 16 is heated by the heating element 17 via the metallic inlay 16. The heated metallic inlay 16 therefore causes a halo of increased temperature in the phantom body 15. The heated part of the background surface 15a is thus clearly distinguishable over the marker surface 16a in the thermal image of the first camera 1. It appears as a ring-shaped object, with a high contrast at its inner circumference and a radial temperature falloff at its outside.

Figure 10:
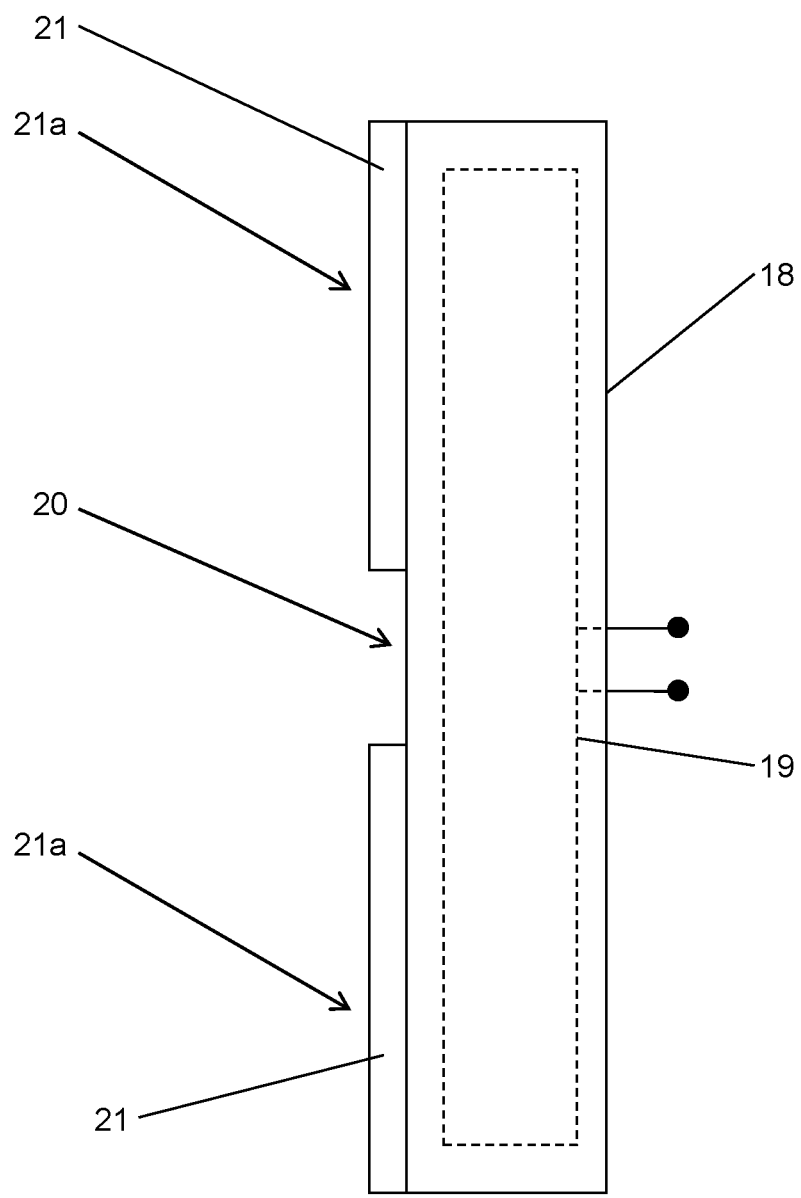

FIG. 10 schematically shows another example of a hybrid phantom. The phantom comprises a metallic phantom body 18, which in turn comprises a heating element 19 in terms of a resistance-heating element 19. A planar surface of the phantom body 18 is covered by a diffuse-reflective coating 21. such as a foil or paint. The coating 21 forms a background surface 21a having a high thermal emissivity and being diffuse reflective for the light emitted by the second camera 2. Openings in the coating 21 expose parts of the planar surface of the phantom body 18. At least those exposed parts are polished and therefore form marker surfaces 20 being specular reflective for light emitted by the second camera 2 and having a low thermal emissivity. The heating element 19 heats the coating 21 via the phantom body 18. Due to the different properties of the background surface 21 a and the marker surfaces 20, they can be clearly distinguished in the thermal image. It is of course possible to provide the coating as marker surfaces and to leave the rest of the polished metal surface of the phantom body 18 exposed. In this case the properties of the background surface and the marker surfaces are inverted.

Instead of being heating elements, elements 17 or 19 can also be cooling elements such as Peltier elements.

The phantom body 13 in FIG. 8 or the phantom body 15 in FIG. 9 can for example be made of polyethylene, such that they form background surfaces 13a and 15a, respectively, with the desired properties.

The invention claimed is:

1. A hybrid phantom comprising:
   a planar surface comprising:
   a background surface having one of a first property and a second property; and
   a plurality of marker surfaces, each marker surface of the plurality of marker surfaces having the other one of the first property and the second property,
   wherein the first property involves having a high thermal emissivity of 0.8 or higher and the second property involves having a low thermal emissivity of 0.2 or less, and
   wherein one of the first property and the second property further involves being diffuse reflective and the other one of the first property and the second property further involves being specular reflective.

2. A method using a system comprising a hybrid phantom, a first, thermal camera, a second, three-dimensional (3D) camera, and a computer, the hybrid phantom comprising:
   a planar surface comprising:
   a background surface having one of a first property and a second property; and
   a plurality of marker surfaces, each marker surface of the plurality of marker surfaces having the other one of the first property and the second property,
   wherein the first property involves having a high thermal emissivity of 0.8 or higher and the second property involves having a low thermal emissivity of 0.2 or less, and
   wherein one of the first property and the second property further involves being diffuse reflective and the other one of the first property and the second property further involves being specular reflective,
   the method comprising:
   capturing, using the first thermal camera, a thermal image of the hybrid phantom;
   identifying, by the computer, an edge of each of the plurality of marker surfaces in the thermal image;
   generating, by the computer, thermal marker locations by identifying locations of each of the plurality of marker surfaces from the identified edges of each of the plurality of marker sufaces;
   capturing, using the second, 3D camera, a 3D point cloud of the hybrid phantom by emitting light onto the hybrid phantom and analyzing reflected light;
   generating, by the computer, 3D marker locations by identifying locations of each of the plurality of marker surfaces from the 3D point cloud captured by the second, 3D camera; and determining, by the computer, a relative position between the first, thermal camera and the second, 3D camera from the thermal marker locations and the 3D marker locations.

3. The method of claim 2, wherein the identifying the edge of each of the plurality of marker surfaces and the identifying the locations of each of the plurality of marker surfaces comprises:
   finding two or more edge pixels lying on a boundary of a respective marker surface;
   calculating a direction of a gradient for each found edge pixel; and
   calculating the location of the marker surface from the directions of the gradients.

4. The method of claim 2, wherein the identifying the locations of each of the plurality of marker surfaces comprises:
   obtaining a two-dimensional (2D) view of the 3D point cloud by rotating the 3D point cloud such that the planar surface of the hybrid phantom is perpendicular to a depth direction of a reference system of the second, 3D camera;
   obtaining auxiliary marker surface locations by identifying the locations of the plurality of marker surfaces in the 2D view of the 3D point cloud; and
   obtaining the locations of each of the plurality of marker surfaces by performing an inverse rotation of the auxiliary marker surface locations.

5. The method of claim 4, wherein a plane is fitted into the points of the 3D point cloud which represent the planar surface of the hybrid phantom, a transformation describing rotations about axes perpendicular to the depth direction of the reference system of the second camera and making the plane perpendicular to the depth direction of the reference system of the second camera is calculated, the transformation is applied to the 3D point cloud and the inverse of the transformation is applied to the auxiliary marker surface locations.

6. The method of claim 5, wherein points of the 3D point cloud which do not lie on the plane are removed from the 3D point cloud.

7. The method of claim 4, wherein the 2D view of the 3D point cloud is a depth map of the rotated 3D point cloud.

8. The method of claim 2, further comprising:
   adjusting the temperature of at least a part of the background surface of the hybrid phantom such that it differs from the ambient temperature.

9. The method of claim 8, wherein the hybrid phantom is cooled using a cooling element or heated using a heating element.

10. The method of claim 8, wherein the hybrid phantom comprises metallic inlays forming the plurality of marker surfaces and the metallic inlays are heated such that their heat dissipates into the background surface surrounding the marker surfaces.

11. A system comprising;
   a hybrid phantom comprising:
      a planar surface comprising:
         a background surface having one of a first property and a second property; and
         a plurality of marker surfaces, each marker surface of the plurality of marker surfaces having the other one of the first property and the second property;
         wherein the first property involves having a high thermal emissivity of 0.8 or higher and the second property involves having a low thermal emissivity of 0.2 or less, and
         wherein one of the first property and the second property further involves being diffuse reflective and the other one of the first property and the second property further involves being specular reflective;
   a first, thermal camera adapted to capture a thermal image of the hybrid phantom;
   a second, three-dimensional (3D) camera adapted to capture a 3D point cloud of the hybrid phantom; and
   a computer configured to:
      identify an edge of each of the plurality of marker surfaces in the thermal image captured by the first thermal camera;
      generate thermal marker locations by identifying locations of each of the plurality of marker surfaces from the identified edge of each of the plurality of marker surfaces in the thermal image;
      generate 3D marker locations by identifying locations of the plurality of marker surfaces from the 3D point cloud captured by the second, 3D camera; and
      determine a relative position between the first thermal camera and the second 3D, camera from the generated thermal marker locations and the generated 3D marker locations.

12. The system of claim 11, further comprising a heating element or a cooling element, wherein the heating element is configured to heat the hybrid phantom or the cooling element is configured to cool the hybrid phantom.

13. The system of claim 11, wherein the hybrid phantom further comprises metallic inlays forming the plurality of marker surfaces, and a heating element wherein the heating element is configured to heat the metallic inlays.

14. The system of claim 13, wherein the metallic inlays are adapted such that when heated their heat dissipates into the background surface surrounding the marker surfaces.

15. The system of claim 11, wherein the identifying the edge of each of the plurality marker surfaces and identifying the locations of each of the plurality of marker surfaces comprises:
   finding two or more edge pixels lying on a boundary of a respective marker surface;
   calculating a direction of a gradient for each found edge pixel; and
   calculating the location of the marker surface from the directions of the gradients.

16. The system of claim 11, wherein the identifying the locations of each of the plurality of marker surfaces comprises:
   obtaining a two-dimensional (2D) view of the 3D point cloud by rotating the 3D point cloud such that the planar surface of the hybrid phantom is perpendicular to a depth direction of a reference system of the second, 3D camera;
   obtaining auxiliary marker surface locations by identifying the locations of the plurality of marker surfaces in the 2D view of the 3D point cloud; and
   obtaining the locations of each of the plurality of marker surfaces by performing an inverse rotation of the auxiliary marker surface locations.

17. The system of claim 16, wherein a plane is fitted into the points of the 3D point cloud which represent the planar surface of the hybrid phantom, a transformation describing rotations about axes perpendicular to the depth direction of the reference system of the second camera and making the plane perpendicular to the depth direction of the reference system of the second camera is calculated, the transformation is applied to the 3D point cloud and the inverse of the transformation is applied to the auxiliary marker surface locations.

18. The system of claim 17, wherein points of the 3D point cloud which do not lie on the plane are removed from the 3D point cloud.

19. The system of claim 16, wherein the 2D view of the 3D point cloud is a depth map of the rotated 3D point cloud.

20. The hybrid phantom of claim 1, further comprising metallic inlays forming the plurality of marker surfaces.

* * * * *